US006461433B1

(12) United States Patent
Carden, Jr. et al.

(10) Patent No.: US 6,461,433 B1
(45) Date of Patent: Oct. 8, 2002

(54) FLUID-JET DEPOSITION OF RADIOACTIVE MATERIAL

(75) Inventors: John L. Carden, Jr., Louvain-la-Neuve (BE); John L. Russell, Jr., Louvain-la-Neuve (BE); James Edward Fox, Royston (GB); Alan Lionel Hudd, Nuthampstead (GB); Michael Willis, Histon (GB)

(73) Assignee: International Brachytherapy, S.A., Seneffe (BE)

( * ) Notice: Subject to any disclaimer, the term of this patent is extended or adjusted under 35 U.S.C. 154(b) by 129 days.

(21) Appl. No.: 09/609,834

(22) Filed: Jul. 5, 2000

Related U.S. Application Data

(62) Division of application No. 09/085,357, filed on May 27, 1998, now Pat. No. 6,086,942.

(51) Int. Cl.[7] .............................. B05C 11/00; B05B 3/00
(52) U.S. Cl. ........................................ 118/688; 118/323
(58) Field of Search ................................. 118/688, 679, 118/680, 681, 323; 427/5, 2.14, 2.11

(56) References Cited

U.S. PATENT DOCUMENTS

| | | | |
|---|---|---|---|
| 3,351,049 A | 11/1967 | Lawrence | 128/1.2 |
| 3,553,708 A | 1/1971 | Carriera et al. | 346/1 |
| 3,811,426 A | 5/1974 | Culver et al. | 128/1.2 |
| 3,832,222 A | 8/1974 | Crisler et al. | 17/107.2 R |
| 4,228,146 A | 10/1980 | Imamura | 424/1 |
| 4,243,694 A | 1/1981 | Mansukhani | 427/14.1 |
| 4,262,206 A | 4/1981 | Viehmann | 250/483 |
| 4,729,903 A | 3/1988 | McGovern et al. | 427/5 |
| 4,756,427 A * | 7/1988 | Gohde et al. | 209/301 |
| 4,877,699 A | 10/1989 | Young et al. | 430/54 |
| 5,132,248 A | 7/1992 | Drummond et al. | 437/173 |
| 5,160,418 A * | 11/1992 | Mullen | 204/153.12 |
| 5,324,359 A * | 6/1994 | Cleveland et al. | 118/688 |

(List continued on next page.)

FOREIGN PATENT DOCUMENTS

| | | | |
|---|---|---|---|
| GB | 1133219 | * | 11/1988 |
| JP | 04037821 A | | 2/1992 |
| JP | 06145727 A | | 5/1994 |

OTHER PUBLICATIONS

Hebner T.R. et al; "Ink–Jet Printing of Doped Polymers for Organic Light Emitting Devices"; Applied Physics Letters vol. 72 No. 5 Feb. 2, 1998; pp. 519–521.

*Primary Examiner*—Richard Crispino
*Assistant Examiner*—Yewebdar T. T.
(74) *Attorney, Agent, or Firm*—Gerry J. Elman; Elman & Associates

(57) ABSTRACT

A method and apparatus for precisely applying radioactive material to a substrate such as a brachytherapy device is disclosed. A radioactive fluid adapted to cure rapidly is deposited as discrete dots onto a surface with a fluid-jet printhead. The apparatus comprises a fluid-jet printhead in communication with a chamber containing radioactive fluid to be applied by the printhead. The printhead is microprocessor driven, and the microprocessor may be provided with feedback from a station where the radioactivity deposited on a preceding substrate in a batch is measured, permitting the system to be recalibrated on an ongoing basis as the batch of printed devices is produced. Compensation for attenuation of radiation by a casing may also be made part of the feedback technique. Also disclosed is a brachytherapy device having printed on a surface dots of radiation-emitting material, in a pattern comprising various bands, dots or areas. Fluids suitable for printing by a fluid-jet printhead comprise a binder such as an acrylic resin or silicate, and a radioactive salt, compound or complex, dissolved in a radiation resistant solvent. Alternative fluids comprise radioactive salts, compounds, or complexes adsorbed onto a microparticulate carrier, or elemental microparticles, dispersed in a rapidly curable radiation-resistant fluid medium.

14 Claims, 9 Drawing Sheets

U.S. PATENT DOCUMENTS

| | | | |
|---|---|---|---|
| 5,342,283 A | 8/1994 | Good | 600/8 |
| 5,389,593 A * | 2/1995 | Holmgren | 502/63 |
| 5,394,816 A | 3/1995 | Kunstat | 114/218 |
| 5,401,535 A * | 3/1995 | Bishop | 427/229 |
| 5,405,309 A | 4/1995 | Carden, Jr. | 600/3 |
| 5,449,754 A | 9/1995 | Nishioka | 530/334 |
| 5,490,962 A | 2/1996 | Cima et al. | 254/22 |
| 5,498,289 A | 3/1996 | Itagaki | 118/401 |
| 5,518,680 A | 5/1996 | Cima et al. | 264/401 |
| 5,558,975 A | 9/1996 | Noguchi et al. | 430/283.1 |
| 5,591,490 A | 1/1997 | Quate | 427/547 |
| 5,643,356 A | 7/1997 | Nohr et al. | 106/31.49 |
| 5,662,809 A * | 9/1997 | Bischoff et al. | 210/757 |
| 5,713,828 A * | 2/1998 | Coniglione | 800/7 |
| 5,882,722 A * | 3/1999 | Kydd | 427/123 |

\* cited by examiner

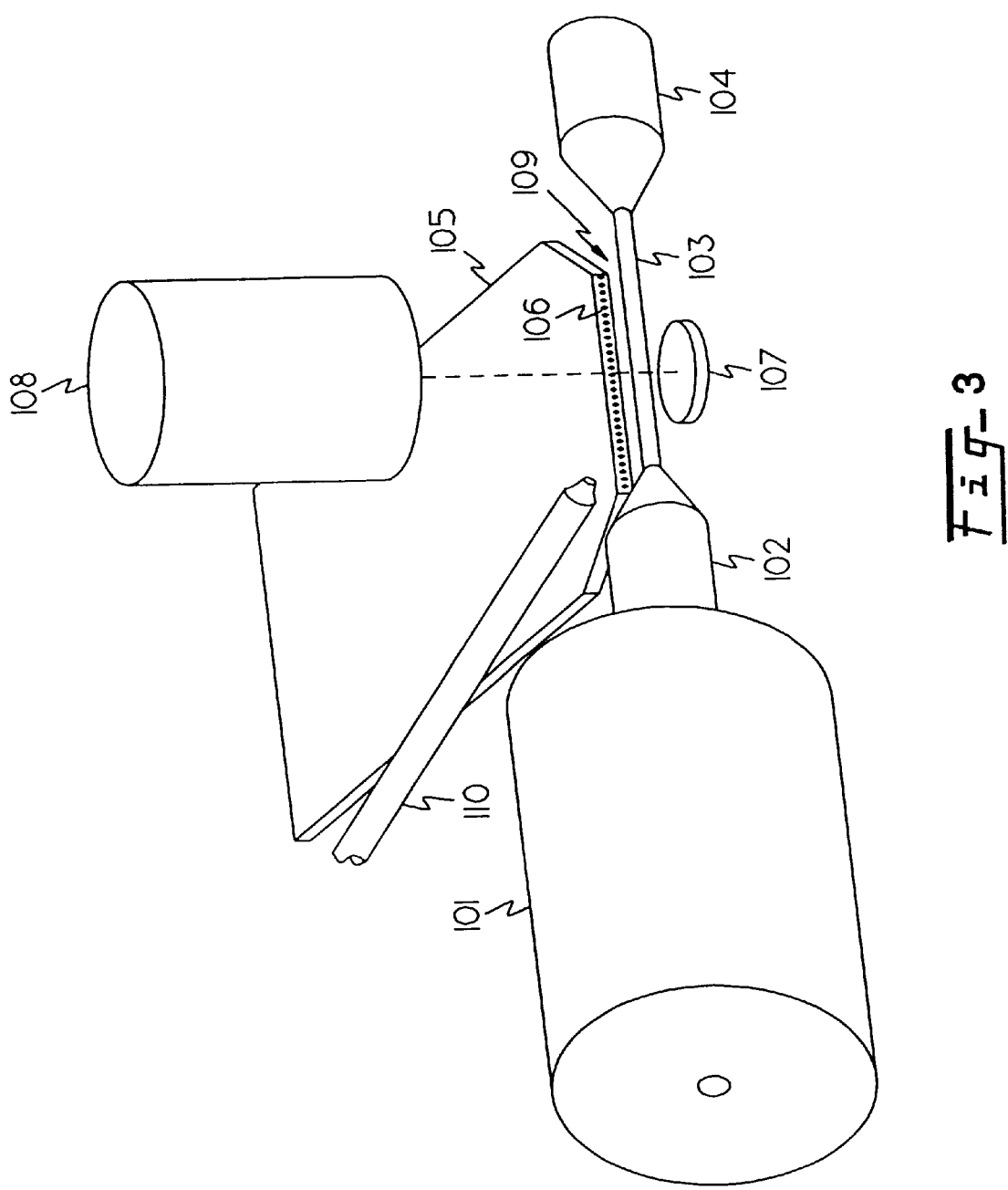

FLUID-JET DEPOSITION OF RADIOACTIVE MATERIAL

RELATED U.S. APPLICATIONS

This is a divisional application of U.S. patent application Ser. No. 09/085,357, filed May 27, 1998, now scheduled to issue on Jul. 11, 2000, as U.S. Pat. No. 6,086,942.

BACKGROUND OF THE INVENTION

1. Field of the Invention

This invention relates to an apparatus and a method for precisely applying radioactive material onto a substrate, e.g. a brachytherapy device or the like. More particularly, the present invention relates to materials and processes for fabricating brachytherapy devices with precisely controlled amounts of radioactive or precursor materials in precisely controlled positions within such devices. The present invention marries two heretofore-disparate technologies, namely those of inkjet printing and of the fabrication of devices for brachytherapy.

2. Description of Related Art

Inkjet printing is used to print a precise amount of ink on a substrate in a precisely defined pattern. Inkjet printheads operate by one of two methods: the so-called, "continuous inkjet" process ("CIJ"), and the "drop-on-demand" process ("DOD"). In DOD inkjet printing, there are two commonly used technologies by which ink droplet ejection is achieved. These technologies are thermal (or bubble-jet) inkjet printing and piezo-electric (or impulse) inkjet printing. In thermal inkjet printing, the energy for ink drop ejection is generated by resistor elements which are electrically heated. Such elements heat rapidly in response to electrical signals controlled by a microprocessor and create a vapor bubble which expels ink through one or more jets associated with the resistor elements. In piezo-electric inkjet printing, ink drops are ejected in response to the vibrations of a piezo-electric crystal. The piezo-electric crystal responds to an electrical signal controlled by a microprocessor.

The localized treatment of tumors and other medical conditions by the interstitial implantation of radioactive materials is a recognized treatment modality of long standing. Radioactive implants are used to provide radiation therapy in order to destroy tumors or reduce or prevent the growth of tumors. Radioactive implants are also used to prevent the growth of microscopic metastatic deposits in lymph nodes that drain the region where a tumor has been removed. Implants are also used to irradiate the postoperative tumor bed after the tumor is excised. Implantation of radioactive sources directly into solid tumors for the destruction of the tumors is used in a therapy referred to as brachytherapy.

For example, U.S. Pat. No. 3,351,049 to Lawrence discloses the use of low-energy X-ray-emitting interstitial implants as brachytherapy sources. Such implants, especially those containing palladium (Pd-103) or iodine (I-125) as the radioactive therapeutic isotope, have proven to be highly effective against solid malignancies. Excellent results have been obtained when such devices have been used against early-stage prostate cancer. These devices, or "seeds," must be very small because they are typically placed in the diseased organ through a hollow needle. Once implanted in the organ, they are held in place by the surrounding tissue or stitched in place with an associated suture. A typical size for a permanent implant is a rod or cylinder 0.8 mm in diameter by 4.5 mm long. A temporary implant is typically inserted into the tissue to be treated through a hollow needle or a plastic sleeve and has approximately the same outside diameter as a permanent implant of about 0.8 mm.

An essential step in the fabrication of these tiny brachytherapy devices is the inclusion in each device of a small amount of a radioactive isotope. U.S. Pat. No. 4,323,055 to Kubiatowicz, U.S. Pat. No. 4,702,228 to Russell, U.S. Pat. No. 5,405,309 to Carden and U.S. Pat. No. 5,713,828 to Coniglione disclose technologies addressing the fabrication of brachytherapy devices. Technology disclosed in the aforementioned patents has been used to develop the processes presently used in the production of commercially available Pd-103 and I-125 seeds. The revenue from the sale of such seeds in the United States in 1997 is estimated to have been about sixty million dollars.

Notwithstanding the commercial success of present methods of brachytherapy device fabrication, the present technology does not provide ways of making brachytherapy devices that contain precisely controlled amounts of radioactive material so as to provide devices for specific orders or to provide treatment tailored to therapy requirements. Nor does it provide ways of making brachytherapy devices that contain precisely positioned amounts of radioactive material so at to provide devices with radiation fields of a controlled shape to meet therapy requirements. Nor does it provide ways of making individually produced brachytherapy devices so as to control wastage of radioactive material and meet the needs of individual customers. Nor does it provide ways of automating production of brachytherapy devices to reduce radiation exposure during manufacture, to reduce the fabrication time and to improve the uniformity of the finished product.

SUMMARY OF THE INVENTION

The inventions disclosed herein include a novel method for fabricating radiation-emitting elements, such as brachytherapy devices, and a brachytherapy device made by the novel method. The method and device disclosed herein provide improvements that can meet the various needs enumerated above.

The present invention provides a novel method for producing a radiation-emitting element consisting of a substrate onto which a radioactive fluid has been deposited in a predetermined pattern and quantity. The fluid is generally solidified (i.e. "cured") such as by polymerization or drying, before the radiation-emitting element is used.

An embodiment of the present invention comprises depositing a predetermined amount and pattern of a radioactive fluid onto a surface of a substrate as drops from a fluid-jet printhead. The technology associated with inkjet printing is generally applicable to the deposition of any fluid, whether or not such a fluid has the properties of an ink. Accordingly the term "fluid-jet" rather than "inkjet" is used herein, though the reader should understand that apparatus and methods used heretofore for inkjet printing may generally be adapted for use with the present invention, as more fully described below. Inkjet printheads reproducibly apply droplets of precise volumes to precise positions on substrates.

In particular embodiments of the present invention, individual drops of a radioactive material are deposited by a fluid-jet printhead in a predetermined pattern. Such a pattern may comprise a plurality of bands, dots or areas.

In a further embodiment of the present invention, a series of radiation-emitting elements are produced in succession, using feedback to fine tune the production of a subsequent deposited substrate based on a measurement from a previous one. The amount of radioactive fluid to be deposited on the present substrate is determined by measuring the amount or pattern of radioactive fluid deposited on a preceding substrate and accordingly adjusting the amount or pattern of radioactive fluid to be applied to the present substrate.

In a further embodiment of the present invention, the substrate has a surface over which a partially radiation-attenuating element is to be secured. This may be the cylindrical outer casing of a hollow seed brachytherapy device such as disclosed in the '828 patent. To compensate for the attenuation of radiation by such an element, one measures the radiation-attenuating properties of the partially radiation-attenuating element; and then computes from that measurement the amount and position of the radioactive fluid to be deposited from the printhead onto the substrate so as to compensate for the measured radiation attenuating properties and thereby produce a desired radiation field external to the casing, or partially radiation-attenuating element. The radioactive fluid from the fluid-jet printhead is then deposited in predetermined amounts at predetermined locations on the surface of the substrate as so computed, and the partially radiation-attenuating element is secured in position. For further precision, the radiation-attenuating characteristics of the substrate itself are similarly measured and taken into account when the radioactive fluid is applied to the substrate.

A radioactive fluid suitable for use in a fluid-jet printhead is also an invention. Such a radioactive fluid comprises a radioisotope, e.g. in the form of a salt, a compound or a complex thereof. The radioisotope may be dissolved in a curable or dryable radiation-resistant solution, or it may be adsorbed onto a dispersible particulate carrier or powder that is dispersed in a curable radiation-resistant solution. "Curable" as used herein means that the fluid solidifies, e.g. by the evaporation of solvent or the forming of a polymer. Such a curable solution preferably includes a binder. Such a binder is a substance that cures to form an organic polymer (a resin) or an inorganic polymer, serving to retain the radioisotope on the substrate surface.

A particular embodiment of the radioactive fluid of the present invention includes a solution of tetraammoniumpalladium(II) hydroxide and acrylic resin in water. By tetraammoniumpalladium(II) hydroxide we mean $(NH_3)_4Pd(OH)_2$. In another embodiment, the radioactive fluid comprises a radioactive powder consisting essentially of a support material onto which a radioisotope is adsorbed. Such a support material may, for example, be carbon black, activated charcoal, silica gel or, in the case of radioactive iodine, a finely ground silver zeolite. Such a radioisotope is preferably radioactive iodine or radioactive palladium. The binder is preferably an acrylic resin. In yet another embodiment, the radioactive fluid comprises a radioactive powder consisting essentially of a radioisotope such as Pd-103 in the form of palladium black (small crystals of metallic palladium) or Y-90 particles.

Various radioisotopes used in the production of brachytherapy devices that emit electro-magnetic radiation (γ-rays or X-rays), β-particles or α-particles are envisaged to be used in the present invention. Examples of such radioisotopes are isotopes that decay principally by electron capture followed by X-ray emission such as palladium-103 and iodine-125; isotopes that decay by the emission of β-particles such as gold-198, gold-199, yttrium-90, and phosphorus-32; isotopes that decay with the emission of β-particles and γ-rays such as iridium-192, and isotopes that decay with the emission of α-particles such as americium-241.

Particles suitable for use in fluid-jets are generally uniform in size and have a maximum dimension not greater than about one-tenth the diameter of the jet aperture. Jet apertures of fluid jet printers are generally about 10 microns in diameter. Accordingly, particulate carriers of powders used in the present invention consist of particles small enough to easily pass through a jet of a fluid-jet printer and generally are less than 1 micron in any dimension.

A wide range of resins which may be used in the current invention are known in the inkjet and surface-coatings industries. These include, but are not limited to, acrylics, styrene acrylics, polyamides, polyvinylbutyrals, polyvinylpyrrolidones, polyketones, polyesters, phenolics, polyvinyl acetate copolymers, and maleic anhydride copolymers.

While the method of the present invention may be applied to any surface onto which it is desired to apply radioactive material, the substrate is preferably a brachytherapy support element and the method produces a brachytherapy device. When the present method is used to make a brachytherapy device, the brachytherapy support element can be of any shape, for example the shape of a tube, a rod, a suture, or a flat, convex, or concave sheet, or a sheet having a cup or bowl shape. Support elements can also be a solid body having the form of any regular or irregular solid, a sphere or an ellipsoid. The method of the present invention is particularly suited to applying radioactive material to the inner-tube of a brachytherapy device such as that disclosed in the '828 patent.

The process of the present invention is used in another embodiment of the invention to deposit a predetermined amount and pattern of an activatable element or isotope, a "precursor material," onto a substrate using a fluid-jet printhead. In such an embodiment of the present invention, individual drops of a non-radioactive material containing an activatable isotope are deposited in a predetermined pattern to produce a precursor device. Such a predetermined pattern may comprise a plurality of bands, dots or areas. In such an embodiment, the precursor device is bombarded by suitable nuclear particles (e.g., neutron irradiation) to transmute, and thereby activate, the activatable isotope into the desired amount of radioactive material.

A non-radioactive fluid suitable for use in the aforesaid embodiment of the present invention comprises a salt, compound or complex of the activatable element or isotope either dissolved in a curable solution, or adsorbed onto a dispersible particulate carrier that is dispersed in a curable solution. The curable solution may include a binder.

A particular embodiment of the non-radioactive fluid of the present invention includes a solution of tetraammoniumpalladium(II) hydroxide and sodium silicate in water.

Precursors of radioisotopes commonly used in the production of brachytherapy precursor devices are also envisaged to be used in the present invention. A precursor isotope such as palladium-102, yttrium-89, gold-197 or iridium-191 as disclosed in the '828 patent can be applied and then transmuted in situ by neutron irradiation.

Brachytherapy precursor devices of the invention, having precursor material on a substrate, which are activated by subsequent bombardment with appropriate nuclear particles, have a material for the substrate that is activated no more than to a minimal degree by the nuclear particles and is not otherwise modified by the radiation field present during activation.

Brachytherapy devices made by the method of the present invention have a brachytherapy support element with radioactive material applied thereon by the method of the present invention. Preferably they additionally have a substantially radiation-transparent sealing element sealingly joined to the support element to seal the surface of the brachytherapy support element and to prevent any release or escape of radioactive material from the device when in use.

Another invention disclosed herein is a brachytherapy device made by the present method. Such a brachytherapy device comprises a brachytherapy support element, radioactive material on the surface thereof, and a sealing layer to enclose and seal in the radioactive material. The support element can have the shape of a tube, a rod, a sheet, a suture, or a solid body having the form of any regular solid, a sphere or an ellipsoid. The radioactive material is applied to the surface of the support element by the process disclosed herein. The radioactive material is in the form of a pattern of a plurality of discretely applied drops of fluid. The plurality of discretely applied drops of fluid is disposed in a predetermined pattern, preferably comprising a plurality of bands, dots or areas.

CIJ technology may alternatively be used instead of DOD technology, to deposit radioactive material onto a substrate. However, if a CIJ printhead is used to implement the process of the present invention, jetted ink that is not deposited on the substrate would be captured for recycling. The high radiation intensity associated with the fluid and the economic value per unit volume are factors to be considered in designing the recycling process.

Another invention disclosed herein is an apparatus for carrying out the method of the present invention. Such an apparatus applies discrete drops of radioactive material onto a surface of a substrate. The apparatus comprises a fluid-jet printhead; a reservoir for a radioactive fluid having an opening communicating with the fluid-jet printhead; means for positioning a substrate relative to the printhead; means for moving the substrate relative to the printhead; a microprocessor that controls the firing action of the printhead and the means that positions the substrate relative to the printhead. Other embodiments of the apparatus of the present invention also incorporate means for "housekeeping" of the printhead (including control of fluid evaporation from the printhead nozzles, nozzle plate cleaning and means for capturing fluid jetted during priming, jet clearing and other printhead maintenance operations) and means for facilitating curing of the deposited fluid. Other embodiments further incorporate an observing means to monitor performance of the printhead.

The preferred apparatus of the present invention comprises a DOD printhead. Advantageous features of DOD printheads include smaller drop volume, reduced waste and the absence of a need to recycle a portion of the jetted fluid. However, both DOD and CIJ techniques are capable of delivering very precise volumes to a substrate in a predetermined pattern. In the present invention, the piezo-electric technique is preferred to the thermal technique because it allows the use of higher viscosity fluids, permitting greater flexibility in fluid formulation. Piezo-electric printheads are also more robust, reducing the possibility of failure from corrosion.

Another embodiment of the apparatus of the present invention also comprises a radiation-measuring device to assess the radioactivity that has been applied to a substrate and means to receive data from the measuring device and feed it to the microprocessor to provide feedback, thereby controlling the amount of radioactive material deposited by the printhead on successive brachytherapy supports.

A further embodiment of the apparatus of the present invention comprises a coating means to apply a substantially radiation-transparent sealing coat over the substrate so as to sealingly enclose the radioactive material.

The present invention has a number of features that provide advantages over previously described methods of making brachytherapy seeds. Particularly, the method disclosed herein allows precise amounts of radioactive material to be applied at an accurately determined position on a surface. When the presently described technique is used to make a brachytherapy device, a resulting device emits an accurately known amount of radiation. The radiation field is determined by the position of the radioactive material present on the device. The shape of the field can therefore be tailored by changing the position or amount of the radioactive material. The method disclosed herein advantageously facilitates such tailoring. Thus, the method disclosed herein advantageously allows radioactive material to be precisely positioned on a brachytherapy support structure so as to make a brachytherapy seed which emits a symmetrical radiation field. Alternatively, the method disclosed herein allows deposition of radioactive material so as to make a brachytherapy seed which emits a deliberately asymmetric radiation field.

A preferred embodiment of the method of the present invention permits accurate determination of the attenuation of emitted radiation by the material components of a hollow-tube brachytherapy device. In such a device, attenuation of emitted radiation, though relatively slight, is principally caused by the outer sealing tube. Additional attenuation is caused by the inner tube upon which the radiation-emitting material is deposited. Accurate determination of attenuation of radiation combined with precise control of the amount and position of radioactive material within the device allows production of brachytherapy devices that precisely meet treatment modality requirements.

In the present method, radioactive material is deposited on individual brachytherapy support structures in a one-at-a-time manner, unlike previously mentioned batch processes of the prior art. Individual production of brachytherapy devices has a therapeutic advantage, in that the actual radioactivity of each device so produced is known. Devices may be readily made by the methods disclosed herein that have particular activities suited for particular purposes. Additionally, devices may be made to fill specific orders, thus avoiding the possibility that the limited quantity of isotope available will be used to produce devices which are not purchased. For example, a physician may specify that a device of a particular activity is to be implanted on a particular day in the near future. Such a device may be produced in accordance with the present invention, with exactly the amount of radioactive material that, after decay to the specified day and time, has the desired value. Accordingly, the method disclosed herein allows precise amounts of radioactive material to be deposited on brachytherapy support structures in a one-at-a-time manner, thus making it possible for the first time to produce devices according to a prescription for a particular patient or application. Additionally, the method disclosed herein allows radioactive material to be precisely positioned on a brachytherapy support structure so as to make a brachytherapy seed which emits a consistent symmetrical or asymmetrical radiation field as required for a particular application.

A further advantage conferred by the present invention allows brachytherapy devices to be manufactured as needed, in accordance with just-in-time manufacturing principles, rather than being batch-produced so as to maintain an inventory against which orders are subsequently placed. The present invention minimizes prior-to-use decay, which is a problem for manufacturers and therapists with present methods of manufacturing brachytherapy devices because of the short radioactive half-life of the most suitable therapeutic isotopes. The present invention thus makes it possible to avoid having an inventory of unused seeds that must be securely stored and that, by radioactive decay, become therapeutically ineffective before they can be used.

These and other objects, advantages and features of the present invention will be apparent from the appended drawings and detailed description.

BRIEF DESCRIPTION OF THE DRAWINGS

FIG. 3 is diagrammatic perspective view of the components of a fluid-jet station of the present invention.

DETAILED DESCRIPTION

In a preferred application of the method of the present invention, drops of material are discretely applied to a surface of a support element of a brachytherapy source. In different embodiments of the invention, the fluid may be radioactive or it may be a precursor material that is activated by nuclear particle bombardment. The radioactive material is preferably applied as a fluid that is compatible with the physical and operational characteristics of a drop on demand ("DOD") inkjet printhead. Because the fluid of the present invention is not intended to be viewed as a black or colored ink printed on paper or like substrate, this disclosure uses the term "fluid-jet" to refer to the technologies conventionally known as "inkjet" or the like. In preferred embodiments of the invention, the printing position for each drop of the fluid to be applied to a brachytherapy support element is determined so that a predetermined amount of a fluid is quantitatively applied in a predetermined pattern.

In accordance with the present method, a brachytherapy support element is positioned at successive predetermined positions in front of the printhead of a fluid-jet printer so that the fluid is applied in a predetermined pattern. In a preferred embodiment of the method of the present invention, measurement of the amount of radioactive material deposited on the brachytherapy seed is done during the manufacturing process, and the information derived is used to adjust the printing parameters so as to keep the product to a desired specification. Measurement is performed immediately following printing, in order to minimize production of out-of-specification sources in the event of an abrupt change in printing performance. It has been found desirable to position the measurement station close to the print station so as to provide timely data about any change in printing performance. In a production line, if the measured property of individual sources produced drifts somewhat from the desired specification, the drift will not be detected until the first of the off-specification sources reaches the measurement station, at which point information about any printing drift would become available for correcting the performance of the print station.

In the method of the present invention, the amount of radioactive material applied to each brachytherapy support element is measured, such as with a radiation monitor. Further, in a preferred method, the measured amount of radioactive material is used to provide feedback control of the quantitative amount of radioactive fluid applied to each successive device.

Figure 1:
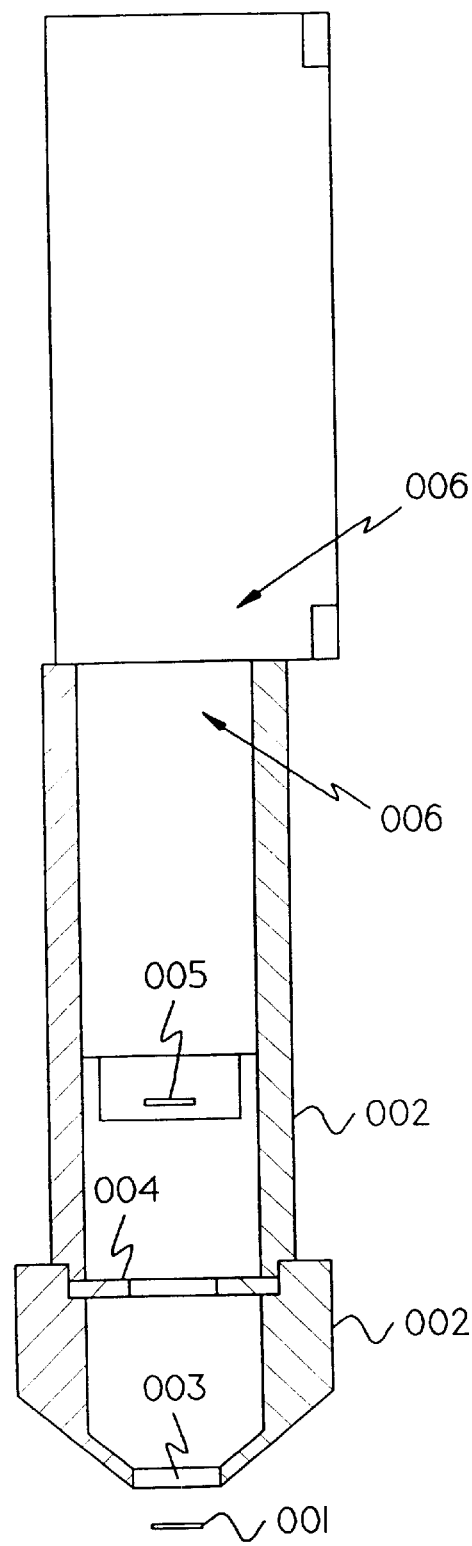
FIG. 1 is a diagram of a cross section of an apparatus for measuring radiation emitted by a brachytherapy seed.

FIG. 1 shows a cross section of an apparatus for measuring the radiation emitted by a brachytherapy seed that comprises a low-energy X-ray emitting radioisotope such as Pd-103 or I-125. As shown, seed 001 is positioned so that emitted radiation passes through aperture 003, through collimator 004, to cadmium-zinc-telluride (CZT) detector 005. Lead shielding 002 protects detector 005 from background radiation. Output of detector 005 is fed to preamplifier electronics package 006.

The method of the present invention may also comprise applying a substantially radiation-transparent sealing layer over the radioactive-material-coated brachytherapy support element, so as to sealingly enclose the radiation-emitting material. In different embodiments of a device made by the method of the present invention, the sealing layer may be a plastic coat, a titanium shell, or other suitable radiation-transparent material.

Preferably, sealing layers used in the present invention are substantially radiation transparent. However, the method of the present invention permits accurate determination of the attenuation of emitted radiation by the material components of a hollow-tube brachytherapy device including sealing layers. Attenuation of radiation is determined by measuring the amount of such radiation that is actually absorbed by an outer tube of such a device, measuring the amount of such radiation that is actually absorbed by an inner tube of such a device, and adjusting the amount and location of the radioactive material deposited in the finished device such that the radiation emitted by the finished device precisely matches a desired specification. A device made in accordance with this embodiment of the invention matches a precise specification designed to meet a treatment plan for a specific application.

Figure 2:
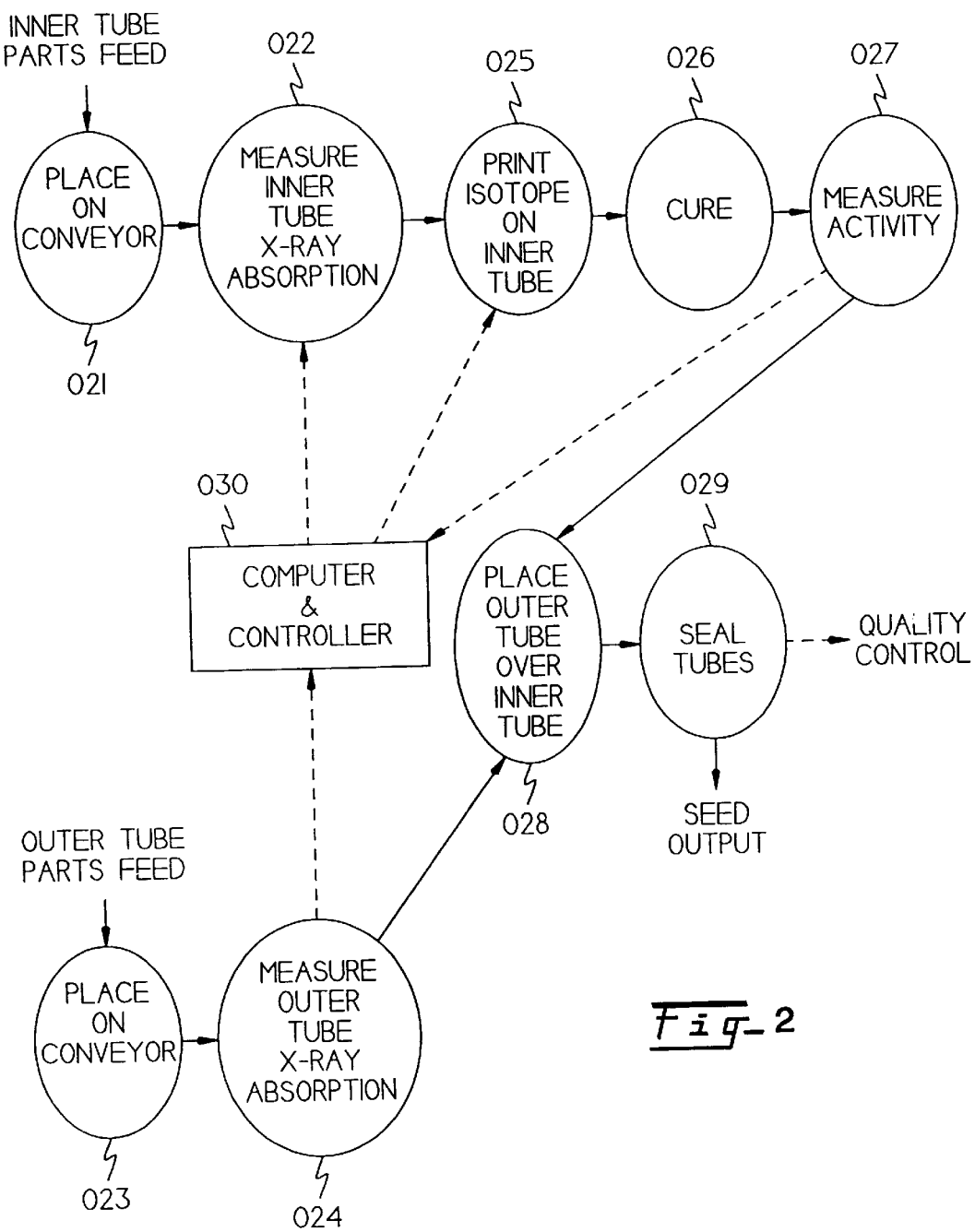
FIG. 2 is a flow chart that diagrams material flow and the data management for control of an apparatus for fluid-jet printing on a substrate.

FIG. 2 is a flow chart that illustrates the flow of parts in an assembly process and the flow of data to a computing means which commands a printhead to print radioactive fluid onto the inner tube of a seed of the type disclosed in the '828 patent. Also shown is the flow of parts and data associated with the assembly of the inner tube and a sealing layer into a finished brachytherapy device. In FIG. 2, data flow is indicated with dashed arrows and material flow is indicated with solid arrows. FIG. 2 shows a diagrammatic representation of the stations of a brachytherapy seed production line. An inner tube is loaded onto a conveyor at loading station 021, and the X-ray absorption by the inner-tube wall is measured at measuring station 022. An outer tube is loaded onto a conveyor at loading station 023, and the X-ray absorption by the outer-tube wall is measured at measuring station 024. The outer tube is then passed to assembly station 028. Radioactive fluid is printed on the surface of the inner tube at printing station 025, the fluid is cured at curing station 026, the activity of the printed tube is measured at radiation measuring station 027 and the printed, cured inner tube is passed to assembly station 028. At assembly station 028 the outer tube is placed over the printed inner tube and the assembly is passed to sealing station 029 where the inner tube is sealingly attached to the outer tube. Quality control is achieved by measuring the properties of finished seeds. Computer 030 receives data from measuring stations 022, 024 and 027 and controls the amount and position of deposition of radioactive fluid at printing station 025. Measuring station 027 comprises two opposed radiation detectors equally spaced from a seed from which the radiation is to be measured. In an embodiment of the present invention wherein Pd-103 is the isotope, cadmium zinc telluride (CZT) detectors are used.

In embodiments of the invention wherein a precursor material is to be activated after deposition of the fluid on the substrate, the sealing layer may be applied before or after the activation process. In an embodiment where the sealing layer is applied before activation, the sealing layer used is capable of retaining its physical properties when exposed to the radiation environment associated with activation and is not itself activated to form significant amounts of any isotopes with a half-life comparable to or longer than that of the deposited isotope.

The invention disclosed herein also contemplates an apparatus for depositing discrete dots of radioactive material onto a surface of a substrate. Such an apparatus comprises: (a) a fluid-jet printhead; (b) a reservoir for radioactive fluid having an opening through which the fluid may flow to the fluid-jet printhead; (c) positioning means for positioning a substrate relative to the printhead; (d) adjusting means to provide relative motion to the printhead and the substrate; and (e) computing means in communication with the printhead and with the adjusting means for establishing the relative positions of the printhead and the substrate, and for controlling firing of the printhead, so as to apply a predetermined amount of radioactive fluid at a specified position on the substrate. To minimize the amount of fluid required, the fluid-reservoir of the print head is closely connected to a manifold that feeds the individual channels of the piezoelectric printhead.

Optionally, an apparatus of the present invention also includes: (f) measuring means for assessing the radioactivity that has been applied to a previously treated substrate; and (g) a second computing means, receptive to data supplied by the measuring means to provide feedback to the first computing means so providing control of the amount of radioactive fluid subsequently deposited by the printhead; (h) a curing means, to dry the deposited fluid by the application of thermal energy in the form of a heated gas, infrared radiation, resistance heating, thermal conduction, etc., or cure the fluid by the application of a reaction-activating catalyst in the form of infrared or ultraviolet light, heat, a reactive chemical in the form of a gas or a liquid applied as a second layer, etc.; (i) a housekeeping means to prevent drying of the entrance of the jets in the printhead, to clean the nozzle plate of the printhead and receiving vessel, and/or to capture radioactive or precursor printing fluid in a receiving vessel during head priming, and (j) an observing means to allow visualization of drops in flight between the printhead and substrate and to allow verification that all energized jets are firing, that the drop trajectory is as anticipated and that the buildup of fluid on the substrate is in the desired location.

An apparatus of the present invention optionally also includes means to apply a substantially radiation-transparent sealing coat over the substrate so as to sealingly enclose the radiation-emitting material deposited thereon.

An apparatus similar to a jeweler's lathe was used to carry out a process of the present invention. The apparatus included the features schematically shown in FIG. 3. As depicted, variable speed motor 101 is mounted to drive driven-spindle 102. Titanium tube 103 is mounted between driven-spindle 102 and free-spindle 104. Printhead 105 is mounted so that printhead nozzle plate 106 is at least 0.1 and not more than 3 mm from the surface of titanium tube 103. Pulsed LED light source 107 is mounted adjacent to gap 109 between printhead-face 106 and titanium tube 103. Monitoring video-camera 108 is mounted to observe drops (not shown) illuminated by LED light source 107 as they fly between printhead nozzle plate 106 and titanium tube 103 across gap 109. LED light source 107 also illuminates the build-up of fluid (not shown) on surface of titanium tube 103. Tube 110 directs a gentle, hot, dry stream of gas onto the printed surface of titanium tube 103 to speed the drying or curing of the printed drops.

The apparatus of FIG. 3 was used in conjunction with an MIT printhead. The MIT printhead used in this embodiment is commercially available from Modular Ink Technology, Stockholm, Sweden (MIT No. 0064B). The 0064B printhead has 64 jet ports of which less than half are used in this example because the array of jet ports on the nozzle plate of the printhead is twice as long as the width of the area to be printed, i.e., 4.3 mm.

Several seeds were printed with the fluid described in Table 1. The rotation rate of the tube being printed was 1,935 rpm (32.3 revolutions per second). For the 0.58-mm diameter tube, the surface was moving past the printhead at about 5.9 cm per second. At this speed the motion of the surface resulted in the drops coalescing into bands around the circumference of the tube, but showed no tendency to throw off the deposited fluid by centrifugal force. The fluid was deposited at a per-jet firing rate of 500 drops per second. 6,045 drops were deposited on the tube in approximately 0.8 seconds utilizing 18 jets. The relatively thick layer of fluid built up by this deposition process had a drying time of about 2 minutes. The drying time of non-overlapping drops of a jettable-fluid of the composition shown in Table 1 printed on a flat titanium metal foil, was measured to be about 2 seconds.

Seeds printed in an experiment with identical printing conditions in which similar seeds were printed with the printing fluid shown in Table 2 had a shorter drying time of about 40 seconds.

TABLE 1

| COMPONENT | WEIGHT PERCENT |
|---|---|
| Joncryl SCX 8078 | 68.06 |
| tetraammoniumpalladium (II) hydroxide (15 mg/ml Pd in 5% ammonia in water) | 29.03 |
| Deionized water | 2.91 |

TABLE 2

| COMPONENT | WEIGHT PERCENT |
|---|---|
| Joncryl SCX 8078 | 15.50 |
| tetraammoniumpalladium (II) hydroxide (30 mg/ml Pd in 5% ammonia in water) | 35.00 |
| Methoxypropanol | 6.10 |
| Deionized water | 43.40 |

A major constituent of the fluids shown in Tables 1 and 2 is an acrylic resin (Joncryl SCX 8078). Solutions of 10% by weight acrylic polymer in ethanol were irradiated with X-rays from an electron linear accelerator to different radiation doses and analyzed to determine the effect of radiation dose on fluid viscosity. Significant change would indicate that the print properties of an acrylic resin-based fluid would degrade over time as a result of the radiation emitted within the ink. Results of the test are shown in Table 3.

| Radiation dose (centigray) | Viscosity (cPs) |
|---|---|
| 0 | 2.27 |
| 5,000,000 | 2.45 |
| 20,000,000 | 2.42 |
| 100,000,000 | 2.42 |

A radioactive jettable-fluid for a 5,000 seed production run would ideally, from a fluid-jet printing perspective, have a volume of 1 ml and contain approximately 5 curies of I-125 or 30 curies of Pd-103. Since, in this example, Pd-103 has an activity six-times that of I-125, the Pd-103 poses the more severe radiation challenge and the radiation dose rate in 1 ml of such a Pd-103-containing fluid, is about 4 million centigrays per hour. In accordance with the data shown in Table 3, a jettable-fluid containing either isotope of the exemplary composition would be expected to retain its "printing" characteristics for at least one day.

The printhead, without the small electronics package that controls the jet firing, was tested for sensitivity to radiation by irradiating it to different degrees. The properties of the irradiated printheads were assessed by the manufacturer to determine whether the mechanical resonance properties of the droplet ejection mechanism were degraded by the radiation treatment and the results are shown in Table 4. The results show that the actuator frequency changed by only 2.4% after exposure to 126,000,000 centigrays. Thus printhead performance was substantially unchanged by the radiation. The radiation dose to the head is about half that experienced by the fluid in the reservoir. Accordingly, a radiation exposure of 126,000,000 centigrays would be reached with a 5,000-seed run, over a time period of about 2.5 days.

TABLE 4

| Radiation Dose (centigray) | Actuator Frequency (kHz) |
|---|---|
| 0 | 1,096 |
| 1,000,000 | 1,106 |
| 6,000,000 | 1,111 |
| 26,000,000 | 1,111 |
| 126,000,000 | 1,122 |

The small solid-state electronics package that is typically attached to the printhead itself and which directs electric pulses to specified jets is possibly the most radiation sensitive component of the print system. A shield placed between the electronic package and the fluid reservoir minimizes radiation exposure of the electronic circuits. For I-125, a 1-mm lead shield suffices. Shields suitable for other isotopes will be known to those of skill in the art.

A preferred embodiment of the device of the present invention is a brachytherapy source, or "seed," wherein radioactive palladium is applied with a fluid-jet printer to the outer surface of an inner tube of a device similar to that disclosed in the '828 patent. An apparatus embodying the fluid-jet process as disclosed herein applies the radioactive material contained in a seed prepared by the method of the present invention. In use, such a brachytherapy seed is used as a permanent implant. Clinically, several of such seeds are inserted interstitially in and around a tumor to produce a radiation field, which decays away with the half-life of the radioactive isotope. For example, in the case of Pd-103 the half-life is 17 days and in the case of I-125 it is 60 days. The process of radioactive decay delivers a therapeutic radiation dose to surrounding diseased tissue such as a tumor.

Figure 4A:
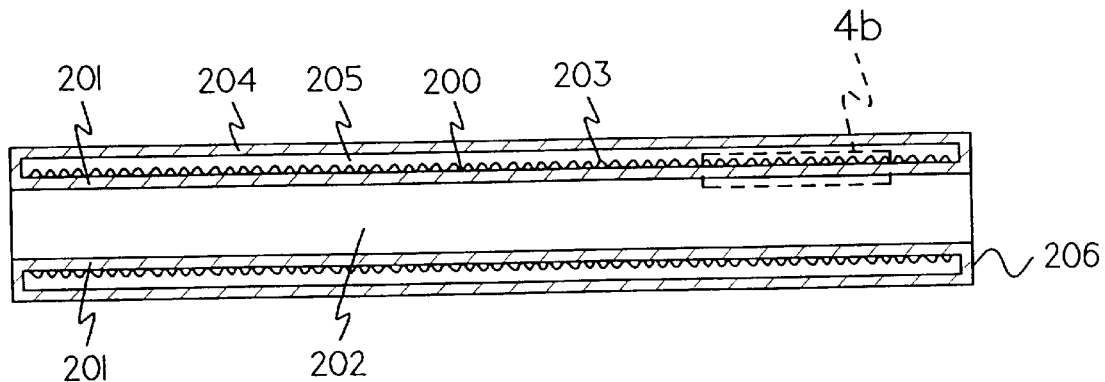
FIG. 4a is a cross-section view of a brachytherapy device of the present invention with a uniform distribution of radioactive material produced by fluid-jet deposition.
Figure 4B:
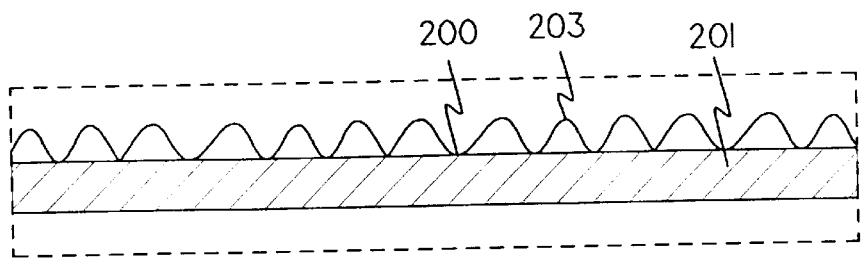
FIG. 4b is an enlargement of the portion of the device shown in FIG. 4a in the area enclosed by broken line 4b.
Figure 5:
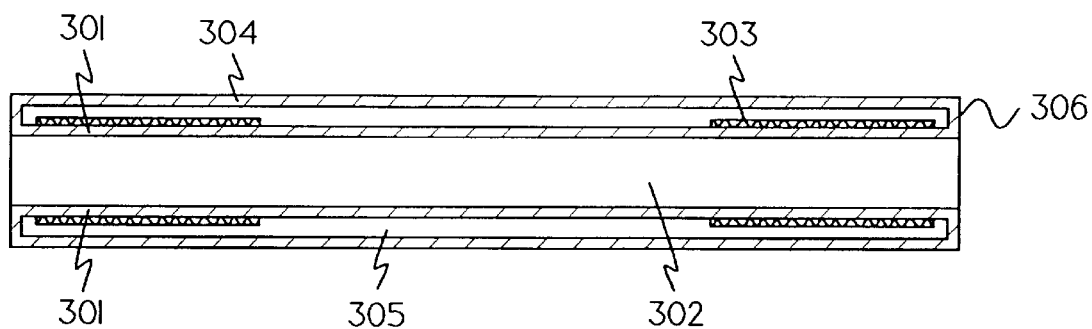
FIG. 5 is a cross section view similar to FIG. 4a of a brachytherapy device of the present invention with a non-uniform distribution of radioactive material.

FIGS. 4a, 4b and 5 show cross-sections of two such hollow-tube seeds and illustrate alternate embodiments of the present invention in which the palladium is differently distributed on the inner tube, e.g., either uniformly as in FIG. 4a, or concentrated near the ends, i.e. "end-loaded," as in FIG. 5. FIG. 4a shows a longitudinal cross section of double-walled hollow seed with radioactive material applied uniformly as discrete drops along the length of the seed. Discretely applied drops, when applied at a sufficient density, fuse to form a series of continuous bands or a film. FIG. 4a shows inner tube 201 with lumen 202 and radioactive material 203 deposited along the length of the outer surface 200 of inner tube 201 as a series of discrete drops. Also shown are outer tube 204 and the space 205 that lies between inner tube 201 and outer tube 204. Welded end 206 is shown sealingly joining inner tube 201 and outer tube 204. FIG. 4b illustrates an enlargement of the region indicated in FIG. 4a showing inner tube 201 and radioactive material 203 on outer surface 200.

FIG. 5 shows a longitudinal cross section of a double-waled hollow seed with radioactive material distributed as two bands near the ends of the seed. FIG. 5 shows inner tube 301 with lumen 302 and radioactive material 303 distributed as two bands near the ends of the outer surface of inner tube 301. Also shown is outer tube 304, space 305 that lies between inner tube 301 and outer tube 304 and the welded end 306 sealingly joining inner tube 301 and outer tube 304.

Figure 6:
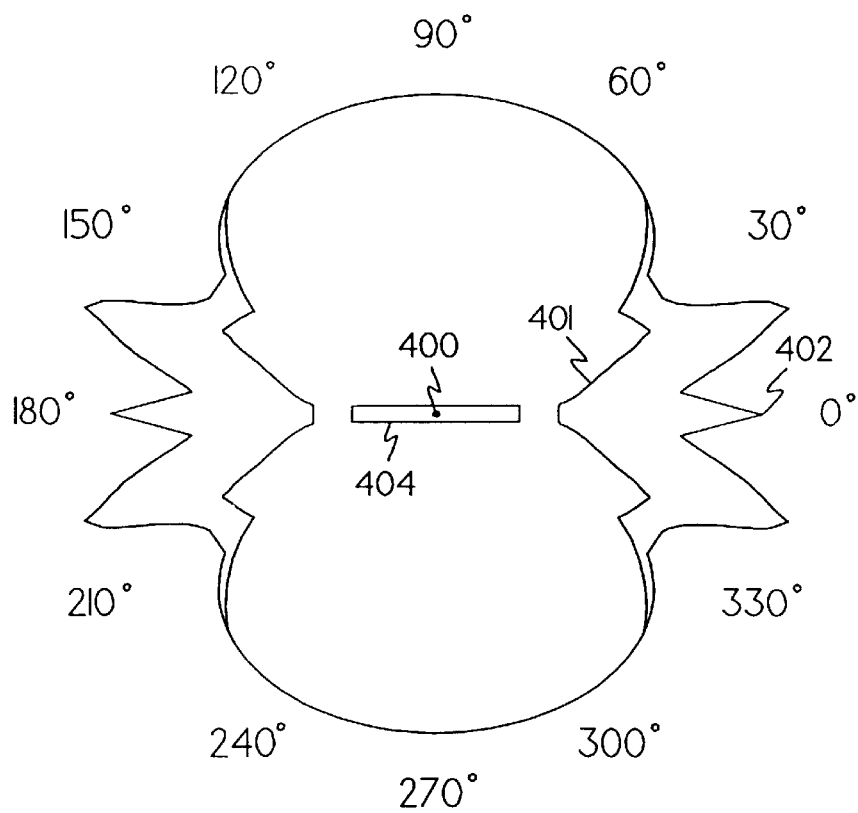
FIG. 6 is a graph illustrating the difference between the radiation fields of the devices shown in FIGS. 4a and 5.

The nonuniform distribution of the radioactive material shown in FIG. 5, produces a more uniform angular distribution of the therapeutic radiation field around the seed, as is illustrated in FIG. 6.

FIG. 6 shows the angular distribution of the radiation field calculated in a plane passing through the longitudinal axis of a brachytherapy seed. In FIG. 6 curves 401 and 402 represent the radiation emitted from each of the seeds exemplified in FIGS. 4a and 5. The distance of curves 401 and 402 from point 400 is proportional to the intensity of the radiation field in that direction at a one cm distance from the point 400 which corresponds to the geometric center of seed 404. The orientation of seed 404 is shown in FIG. 6 centered on point 400. Curve 401 represents the calculated dose rate for radioactive material that is uniformly distributed along the length of the outer surface of the inner tube, as shown in FIG. 4a. Curve 402 represents the calculated dose rate for radioactive material that is distributed as two bands near the ends of the outer surface of an inner tube, as shown in FIG. 5. FIG. 6 illustrates that the ability to distribute radioactive material differentially along the length of the seed makes it possible to modify the shape of the radiation field around the seed and therefore provides a design variable that can be used, along with other seed design parameters, by those skilled in the art to optimize medical effectiveness. In this illustrative example, the minimum dose rate at the 10-deg. angle is 61% higher for the end-loaded seed design, shown in FIG. 5, than that of the uniformly loaded seed shown in FIG. 4a.

The invention disclosed herein comprises a novel use of the inkjet technology to deposit a radioactive fluid onto a medical device. Accordingly, the use of a fluid-jet principle to deposit radioactive material on very small radioactive medical devices has presented unique problems which do not arise in previously disclosed applications of inkjet technology, and which have required the development of certain innovations.

Print patterns have been designed which yield a medically optimal radiation field around the radiotherapeutic device.

Optimal volumes for the jettable fluid have been determined taking into account the mass of the radioactive element present, the solubility of the compound containing the radioisotope in the solvent used, the jetted volume per device that will yield the desired type of deposit (discrete drops or coalesced drops) and the ratio of the initial volume of the jetted fluid to the final dried or cured volume.

A radioactive jettable-fluid has been designed which has the required physical properties and stability to be jetted by a fluid-jet printhead without clogging, weeping, de-priming or otherwise affecting the performance of the printhead.

Radioactive fluids disclosed herein have been developed which dry or solidify quickly after application.

The physical properties of the fluid, such as viscosity, surface tension, wetting, adherence and volatility, have been addressed to ensure that they are not degraded in the course of a production run by the intense radiation field in the radioactive fluid.

The fluid-reservoir and the tubing carrying the fluid have been specially designed to be very closely connected to the printhead channels and to minimize extraneous fluid retention because the radioactive fluid has a very high economic value and a very small volume.

A specially designed medical-device-handler has been developed that positions the surface of the very small brachytherapy substrate very nearly in contact with the printhead to minimize throw distance between the jets and printing surface so as to ensure good drop placement and spatial resolution in the printed pattern.

Specially designed shielding has been developed and positioned so that radiation emitted from a completed device can be monitored adjacent to the printhead and its reservoir of radioactive fluid.

An algorithm and a computer program have been developed to control the print pattern and modulate it in response to a signal derived from the measured radiation emitted from a device shortly after the radioactive material has been applied.

A protective coating has been developed that is applied during manufacture to protect the radioactive printed surface from abrasion or other damage during use, thus preventing escape of the radioactive material.

Printing fluids suitable for use in embodiments of the present invention for printing radioactive or precursor materials with a fluid-jet printhead comprise either a radioactive isotope or a precursor isotope, a carrier solvent that may be a blend of solvents and additives, together with a binder.

A radioactive isotope or precursor isotope suitable for use in a fluid of the present invention may have a form of: a) a water soluble salt, complex or compound of the element such as tetraammoniumpalladium(II) hydroxide or palladium chloride; b) a salt, complex or compound of the element, such as palladium acetate or palladium iodide that is soluble in an organic solvent; c) an insoluble salt, complex or compound of the element, such as yttrium oxide, dispersed in an aqueous or organic medium; d) elemental particles, such as small particles or crystals of palladium metal, dispersed in an aqueous or organic medium; or, e) the isotope, the isotope plus carrier (the naturally occurring form of the element of the isotope) or a compound, complex or salt of the isotope adsorbed or chemisorbed onto a particulate which is dispersed in an aqueous or organic medium.

Materials suitable for use as particles in the present invention include carbon black, activated charcoal, silica gel, and silver zeolites. For use in the present invention, such materials have, or are ground to have, substantially uniform particles of about 1 micron or less. Radioactive isotopes or precursor isotopes may be adsorbed or bound to such powders or particulate materials by covalent, ionic, or van der Waals forces, or may be chemisorbed to such particles. For example, I-125 may be adsorbed onto finely ground charcoal dispersed in water with a surfactant.

The radioactive material is incorporated at a concentration suitable for printing the desired activity and in a volume that is the preferred compromise between an acceptable drying time and the cost of lost radioactive or precursor material associated with dead volume and other losses in the printing system.

A carrier solvent, or blend of solvents, suitable for use in a fluid of the present invention has properties that fulfill the following requirements: a) irradiation from the contained radioactivity does not modify the solvent properties so that printing becomes unreliable in embodiments of the invention that print radioactive material; b) for a DOD printing system, the fluid surface tension is greater than 25 dynes/cm, more preferably greater than 27 dynes/cm and most preferably equal to 29 dynes/cm; c) for an MIT printhead (as disclosed above) the viscosity is preferably from 3 to 10 cPs and more preferably between 5 and 8 cPs; and, d) the fluid dries or cures on printing within an acceptable time without causing clogging of the printhead nozzles.

Suitable drying solvents are liquids such as water or organic solvents such as alcohols, ketones, esters, or glycols. Curing carriers may be used as the solvent either alone or in combination with other carriers. Such curing carriers consist of unsaturated monomers such as N-vinyl pyrrolidone, or reactive oligomers.

A binder suitable for use in a fluid of the present invention has the following properties: a) it is sufficiently radiation resistant so that the absorbed radiation dose does not alter the properties of the binder enough to prevent reliable printing or compromise the desired end user properties; b) it exhibits good adhesion to the substrate surface and sufficient abrasion resistance when dry to prevent damage to the deposited layer during the subsequent manufacturing steps; c) it provides the desired solution viscosity when mixed with the solvent and other solution components; and, d) it retains the radioactive material in the as-deposited location throughout the working life of the device.

Sodium silicate is an example of an inorganic binder. Examples of organic resins include acrylics, styrene acrylics, polyamides, polyvinylbutyrals, polyvinylpyrrolidones, polyketones, polyesters, phenolics, polyvinyl acetate copolymers, and maleic anhydride copolymers.

Special considerations come into play for fluids used with precursor isotopes that are to be activated by subsequently-applied neutron irradiation: a) activation of isotopes contained in solvents, binders, etc., by the particles used to transmute the precursor isotope must either result in the creation of sufficiently little radioactivity to deliver a negligible dose relative to that from the therapeutic isotope, or such activated components must have a very short half-life relative to that of the therapeutic isotope so that only the therapeutic isotope remains at significant levels when the device is used; and b) binders used must also be chosen such that all their desired properties survive the intense radiation present during transmutation of the precursor material. Sodium silicate is an example of a suitable binder for use in these embodiments of the invention. The as-dried structure of sodium silicate is radiation resistant and, while activation of the sodium it contains can be significant, the short half-life of the radioactive sodium so generated makes the binder acceptable with precursor isotopes such as Pd-102. Water is an example of a solvent that meets the radiation resistance and compatibility requirements for fluids used to print transmutable materials.

In accordance with preferred methods of the present invention, the steps of applying radioactive material to a device are closely controlled. For example, the firing of individual jets of the fluid-jet printhead is digitally controlled and the vertical and angular positions of the substrate on the positioning means are set by mechanisms which are driven by digitally controlled stepping motors. Additionally, the number and location of drops printed on each seed are precisely specified by a microprocessor as printing is done.

Preferably, the amount of radioactive material printed on each seed is immediately determined to assess whether the programmed printing is producing seeds with the desired radiation strength. A computer program uses the measured amount of radioactivity to determine and automatically adjust the position and number of radioactive drops applied to seeds to be subsequently printed. Thus, embodiments of the invention achieve a production process regulated by active feedback instrumentation to produce seeds of a prescribed activity and radiation-field shape. Where such a process produces seeds, the activity of each individual seed is very precisely controlled.

A printhead, as used in the present invention, generally has an array of nozzles or jet ports, each separately controllable by a microprocessor. In accordance with the present invention, the controlled jets are programmed to precisely position jetted drops of radioactive material onto a substrate. Desirably, automatic handling equipment places the substrate, i.e. a device to which radioactive material is to be applied, in front of the fluid-jet printhead and repositions the substrate after each time the jets have fired. This results in a programmed pattern of drops on the target surface of the substrate and therefore a predictable distribution of radiation from the device.

Typically, the deposited radioactive surface is not sufficiently durable to remain exposed during use, i.e., when implanted into a patient. Therefore it is usually protected with an essentially radiation-transparent covering. The type and properties of the covering depend upon the specific device and the application to which the device is to be put. For example, the seed disclosed in the '828 patent has an outer tube that is welded to the inner tube at the ends, so as to contain the radioactive material between the two concentric tubes and provide adequate protection of the radioactive surface.

When used in conjunction with sealing layers transparent to visible light, as disclosed in the '828 patent, the present invention also allows simultaneous application of colored ink and radioactive materials to achieve color coding of brachytherapy devices so as to facilitate inventory and stock control at production facilities and medical facilities. It is also envisaged that inkjet printing could be used in conventional ways to color code or otherwise mark the outer surface of devices with nontransparent sealing layers to the same end.

The present invention also advantageously uses commercially available (off-the-shelf) parts for CIJ or DOD printers. Use of such mass-produced parts obviates the need to design and fabricate sophisticated close-tolerance parts that might otherwise be prohibitively expensive to produce.

Examples of printheads and suitable jettable solutions are as follows:

Drop on demand (DOD) piezo-electric printheads suitable for use with fluids having a viscosity between 6 and 12 cPs. For example, printheads manufactured by Xaar Limited of Cambridge, United Kingdom; Trident printheads such as ULTRAJET or MICROCODER; and MIT printheads. Table 5 shows the composition of an exemplary printing fluid.

TABLE 5

| COMPONENT | WEIGHT PERCENT |
| --- | --- |
| Joncryl 611 | 16.80 |
| Palladium acetate | 1.05 |
| Methoxypropyl acetate | 82.15 |

DOD, piezo-electric printheads suitable for use with fluids having a viscosity of about 2.5 cPs. For example, printheads manufactured by Epson. Table 6 shows the composition of an exemplary printing fluid.

TABLE 6

| COMPONENT | WEIGHT PERCENT |
| --- | --- |
| Joncryl SCX 8085 | 12.00 |
| tetraammoniumpalladium (II) hydroxide (30 mg/ml Pd in 5% ammonia in water) | 35.00 |
| Surfynol 104E | 0.40 |
| Glycerol | 4.00 |
| Water | 48.60 |

DOD thermal printheads suitable for use with fluids having a viscosity of 1.5 cPs. For example, printheads manufactured by Hewlett-Packard and Canon. Table 7 shows the composition of an exemplary printing fluid.

TABLE 7

| COMPONENT | WEIGHT PERCENT |
| --- | --- |
| Joncryl SCX 8085 | 5.00 |
| tetraammoniumpalladium (II) hydroxide (30 mg/ml Pd in 5% ammonia in water) | 35.00 |
| Diethyl glycol | 6.00 |
| Deionized water | 54.00 |

EXAMPLES:

Examples of various aspects of the invention are disclosed below for illustrative purposes. The following examples illustrate different features of the present invention.

Example 1

In this example, a tetraammoniumpalladium(II) hydroxide is dissolved in ammonia solution and the resulting solution is mixed with a printing base to yield a jettable fluid having properties of viscosity, surface tension and evaporation rate such that the fluid can be reliably jetted. Other salts, solvents and bases can be used, as illustrated in Tables 5, 6 and 7, and those of skill in the art will appreciate that other formulations will have physical properties and chemical compositions suitable for use with particular printheads.

In this embodiment of the present invention a jettable fluid is used in which a tetraammoniumpalladium(II) hydroxide is dissolved in a commercially available resin solution (Joncryl SCX 8078, from S.C. Johnson Polymers BV, Herenvecn, Netherlands), in proportions shown in Table 1. In this solution, 32% of the Joncryl SCX 8078 is comprised of dissolved solids. Therefore, the volume of the printed surface, after drying, is 21% of the jetted volume, not counting the negligible contribution from the palladium salt.

Example 2

In this example, the method of the present invention was used to apply palladium containing material to an inner tube of a hollow-tube seed device such as that disclosed in the '828 patent. Such devices are as shown in FIGS. 4a, 4b and 5. The outer surface of an inner tube of such a device, on which palladium containing material is deposited, is 0.59 mm in diameter and 4.5 mm long. Thus, the surface on which the palladium containing material is applied has an area of 8.325 square mm. A MIT printhead such as that described herein has 32 jets along a length corresponding to that of an inner tube. Thus, if all 32 jets are fired at a rate of 500 pulses per second while the inner tube is rotated at 1,935 revolutions per minute, a total of 496 drops can be applied to the tube during a single rotation.

Example 3

Radioactive material on a seed produced by the method of the present invention is distributed in accordance with a pre-made design. Seed design constraints include that the radioactive material is deposited uniformly around the circumference of a device and that the radioactive material has a specified distribution along the length of the device. The total amount of radioactive material in a seed is determined by the application for which the seed is designed.

An example of a radioactive printing fluid of this invention would be a formulation of Table 1 with approximately 30 Curie of Pd-103 included therein. In such a solution, on an atomic basis approximately 7% of the palladium atoms present are Pd-103 and the remainder would be comprised of the isotopic mixture characterizing natural palladium. The MIT printhead produces drops of volume approximately 33 picoliter, and approximately 6,045 such drops can be used to produce a radioactive seed. If a particular application requires a seed of 6-millicurie activity, then approximately 5,000 such seeds can be produced from a printing fluid containing about 30 Curie of activity. If 6,045 drops are deposited on each seed, the total volume of the printing fluid is approximately 1 milliliter.

Figure 7:
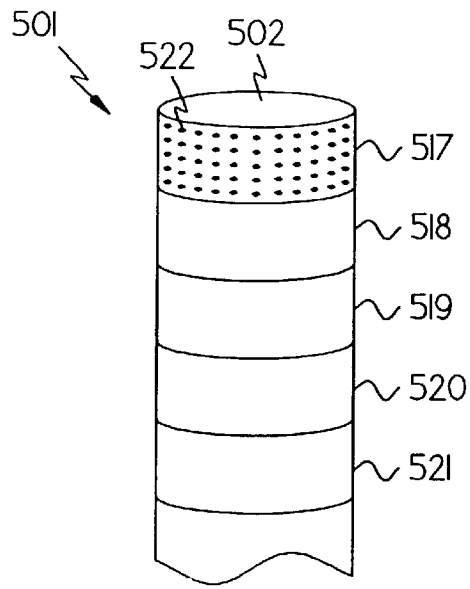
FIG. 7 is a diagrammatic perspective view of a cylindrical brachytherapy device of the present invention, showing a particular distribution of radioactive material thereon.

For the seed design shown in FIG. 7, the radioactive material is concentrated near the ends of the inner tube in bands that are approximately 1 mm wide. Utilizing the MIT printhead described above, 7 jets can be used to form each band. If 6,000 drops are to be deposited, 3,000 in each band, and the jets are fired at a rate of 500 times per second, approximately 0.9 seconds are required per seed. If the seed is rotating at a rate of 1,900 revolutions per minute, approximately 27 layers of drops are deposited in each band.

FIG. 7 shows a design for a seed having five bands of radioactive material. In such a seed, the radioactive material can be distributed in a particular manner, for example the activities of the bands may be in the ratio of 3:2:1:2:3. The total radioactivity for the seed may also be specified as determined by the intended application, e.g., 6 millicurie. In each band the material is deposited as a series of drops applied on a series of bands around the seed.

FIG. 7 is an enlarged diagram that shows a view of the end of an inner tube 501 of a hollow seed showing the location of lumen 502 and radioactive material 522 printed on inner tube 501. The first band 517, second band 518, third band 519, fourth band 520 and fifth band 521, of radioactive material are illustrated. A possible distribution of dots of radioactive material 522 in first band 517 is shown.

The seed of FIG. 7 can be prepared as follows: If an inner tube of the '828 patent of length 4.5 mm is rotated at 1,900 revolutions per minute in the apparatus of FIG. 3 utilizing a MIT printhead, then 32 jets are available for drop generation. If the jets along the length of the seed are numbered consecutively, then the 5 bands of this example can be generated using the following jet pattern: empty band, jet 1; first band, jets 2 to 7; empty band, jet 8; second band, jets 9 to 13; empty band, jet 14; band, jets 15 to 18; empty band, jet 19; fourth band, jets 20 to 24; empty band, jet 25; fifth band, jets 26 to 31; empty band, jet 32. Assuming 6,000 drops are required to deliver the design activity of 6 millicurie, the bands can contain the following numbers of drops: bands 1 and 5, 1,635 each; bands 2 and 4, 1,090 each and band 3, 545. Note that this drop pattern only delivers 5,995 drops, thus assuming all drops have the same volume, it introduces an error of 0.08% in the activity. To deliver the required drops, the jets of bands 1 and 5 must be fired 272 times each, the jets of bands 2 and 4 must be fired 218 times each and those of band 3, 136 times each. If this simple algorithm was followed, only 5,988 drops would be delivered introducing an activity error of 0.2%. This inaccuracy can be compensated for by completing one additional jetting cycle during which only the required jets are fired to deposit a compensating amount of material.

Since the jets of bands 1 and 5 require the largest number of firings, if these jets are fired at 500 cycles per second, the total printing time required is 0.55 seconds. Using software and control electronics provided by MIT, a seed of FIG. 7 is easily prepared.

The actual number of drops required to produce a seed of a specified activity obviously depends upon the radioactivity per unit volume of printing fluid. As will be obvious to anyone skilled in the field, an aliquot of the printing fluid can be assayed by an appropriate technique (e.g., by measurement with a properly calibrated germanium, sodium iodide or cadmium zinc telluride (CZT) detector Pd-103). Using this initial assay and an estimated drop volume (33 picoliter for an MIT printhead), a preliminary estimate of the activity deposited per drop can be obtained. This quantity can then be used to estimate the number of drops that must be deposited to produce a seed of the desired activity. With this estimated number of drops and a drop distribution specification such as that in FIG. 7, a seed could then be prepared by depositing the required number of drops onto the inner tube. This inner tube can then be assayed to determine the amount of activity actually deposited. Since the number of drops actually deposited is known, a more accurate estimate of the activity per drop can be obtained. This process of refining the estimate of activity per drop can be continued until a seed with the desired activity is produced.

As is normal in the industry, the MIT printhead is supplied along with a microprocessor interface card and software that allows microprocessor control of the jet-firing pattern and rate. Utilizing these tools plus computer programming skills that are commonly available, a microprocessor can be used to control the deposition process to achieve the activity and distribution pattern desired on a seed. Once the correct number of drops to produce a seed of desired activity is known, the correct activity can be maintained by measuring the actual activity deposited onto an inner tube and using this information to make appropriate corrections to the number of drops deposited onto the next inner tube. As with all feedback control strategies, appropriate correction requires algorithms that minimize the potential for over correction or oscillation in the activity observed in subsequent inner tubes.

Figure 8:
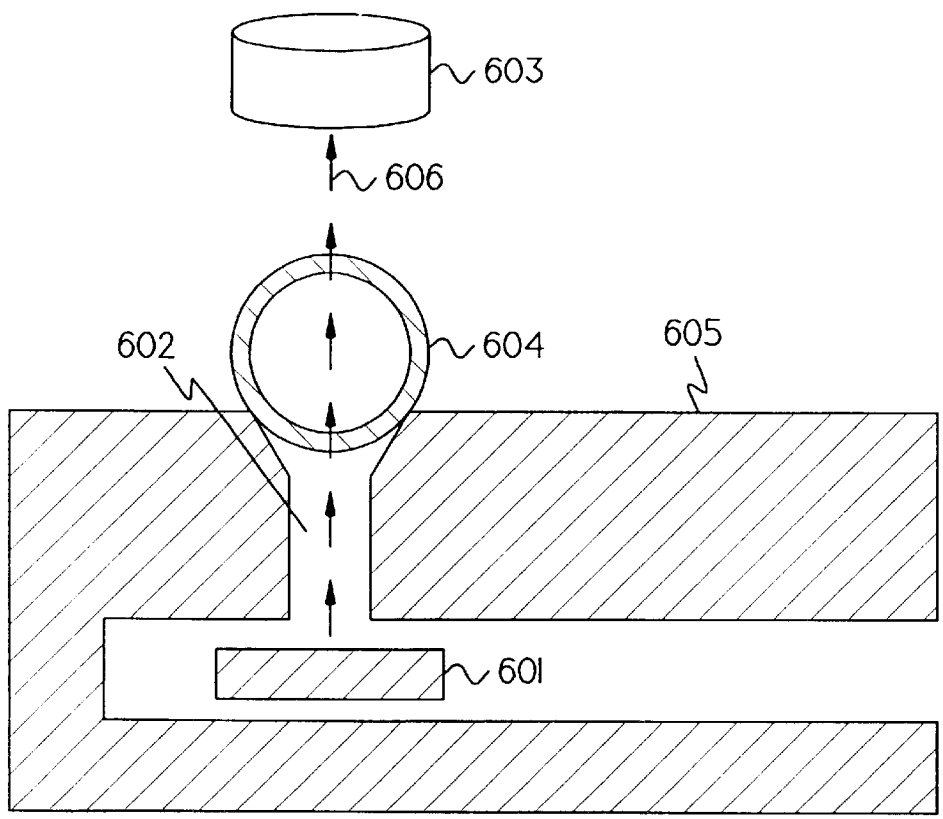
FIG. 8 is a diagrammatic cross-sectional view of an X-ray absorption apparatus for characterization of outer-tube portions of brachytherapy seeds.

Obviously, the shape and strength of the radiation field around a finished seed are the quantities that must ultimately be controlled if the desired product is to be obtained. The shape of the radiation field is determined by the pattern into which the radioactive material is deposited on the inner tube and is consequently simple to control using the techniques disclosed in this invention. The seed strength, i.e., the intensity of the therapeutic radiation field observed around the outside of the finished seed, poses a more complex control problem. Assaying the radioactivity of the as deposited layer provides a means to readily control the deposition process. A finished metal seed of the '828 patent includes an outer tube that is slid over the radioactive material bearing inner tube. This outer tube adds an additional variable because a significant fraction of the radiation emitted from the deposit can be absorbed in the metal of the outer tube. For example, a Pd-103 seed made with titanium tubing as described in the '828 patent can experience absorption of 30% to 50% of the Pd-103 X-rays in the outer titanium tube. Also, small variations in the wall thickness of the outer tube lead to variations in radiation absorption, adding to variability in the strength of the finished seed. The deposition method disclosed in this patent provides a simple way of overcoming variability of X-ray emission caused by variability of X-ray absorption in the outer tube resulting from variations in wall thickness. A low energy X-ray source made from either the same isotope as that of the seeds being fabricated or another isotope such as cadmium-109 is placed into an absorption measurement apparatus such as that shown in FIG. 8. X-rays 606 from source 601 exit through slit 602, pass through outer tube 604 positioned in locating and shielding means 605, and into detector 603, where the intensity of X-rays 606 is measured. Detector 603 can be a CZT detector. The X-ray flux at detector 603 in the presence and in the absence of outer tube 604 is compared to determine the attenuation caused by the walls of outer tube 604. A correlation between outer tube absorption and final seed strength is then established by building finished seeds using inner tubes of known radioactivity and outer tubes of known absorption. This correlation is then used to modify the amount of activity applied to an inner tube that is to be mated with an outer tube of known absorption.

Emission of radiation from an isotope occurs in a spherically symmetrical manner. Accordingly, a proportion of the emitted radiation passes through the substrate upon which the radioactive material is deposited. Variations in the measured intensity of emitted radiation thus occur because of variations in the radiation absorption properties of substrates upon which radioactive material is deposited and variations in the radiation absorption properties of the sealing layers. These variations give rise to differential absorption of the emitted radiation. The attenuation of emitted radiation by the material on which it is deposited and by sealing layers is measured in one embodiment of the method of the present invention with the absorption measurement apparatus described above.

Example 4

The present invention may also be used to apply radioactive material to the surface of a surgical suture.

Figure 9:
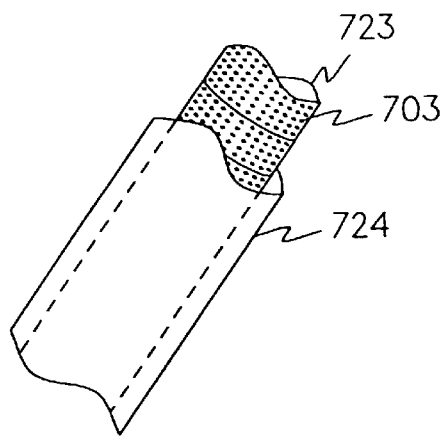
FIG. 9 is a fragmentary perspective view of a brachytherapy device of the present invention.

This example describes a new type of brachytherapy device in which the radioactive isotope is incorporated in a strand of plastic material. Such a radioactive strand can be implanted much as a surgical suture, or cut into sections and implanted as are seeds. Such strands can be made either of a permanent plastic or of a biodegradable plastic. In the latter embodiment, after the radioactive isotope decays to a biologically acceptable level, the strand is dissolved by the body. The radiation field around such a device is substantially uniform along lines parallel to the strand. FIG. 9 is a diagram of a section of a strand of plastic material as exemplified in this example. Strand core 723 is shown together with the layer of radioactive material 703 and protective coating 724. In this embodiment of the present invention strand core 723 and radioactive material 703 have a diameter of about 0.5 mm though other diameters within the spirit of the invention will be known to those of skill in the art. The diameter of strand 723, radioactive material 703 and protective coating 724 thereon illustrated in FIG. 9, is about 0.8 mm. Those of skill in the art will know of other dimensions within the spirit of the invention.

Figure 10:
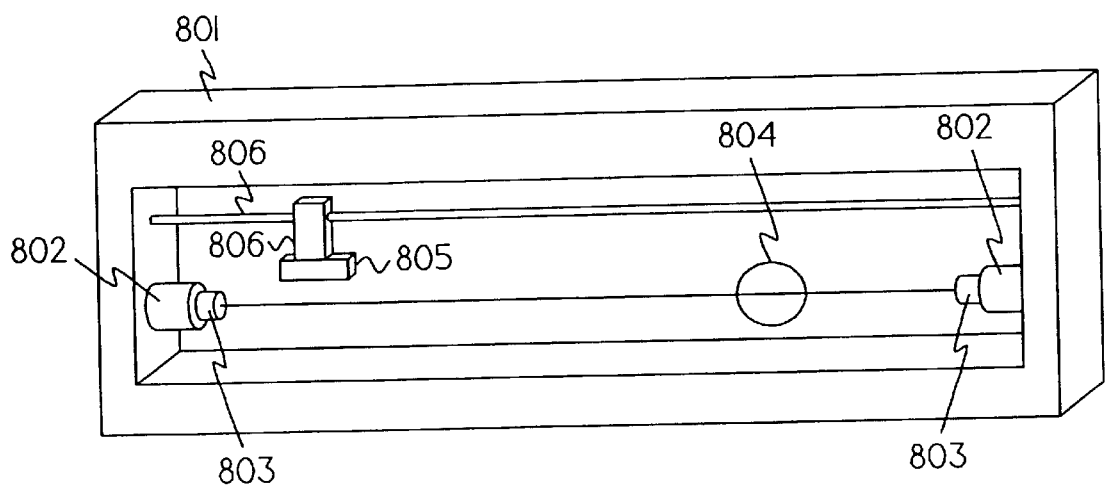
FIG. 10 is a schematic perspective view of an apparatus for deposition of radioactive fluid on sutures for making brachytherapy sources in accordance with the present invention.

Within the spirit of this invention, the apparatus illustrated in FIG. 10 can be used to produce such a radioactive strand. Mounted on rigid support 801 are synchronous motors 802 with chucks and tensioning means 803 holding strand core 804 under tension while rotating it. Printhead 805 with attached fluid reservoir (not shown) is attached to translation means 806 so that it can be positioned at any desired location along strand core 804. Optionally, this apparatus may also incorporate an observing means such as a monitoring video camera to verify printhead performance, a drying or curing means such as an air or heat source to speed the drying or curing process and an assay means to evaluate the radioactivity deposited onto the strand core. If present, such an assay means provides a method for producing strand of a predetermined activity by successively depositing activity and assaying, providing feedback until the desired activity is reached.

Figure 11:
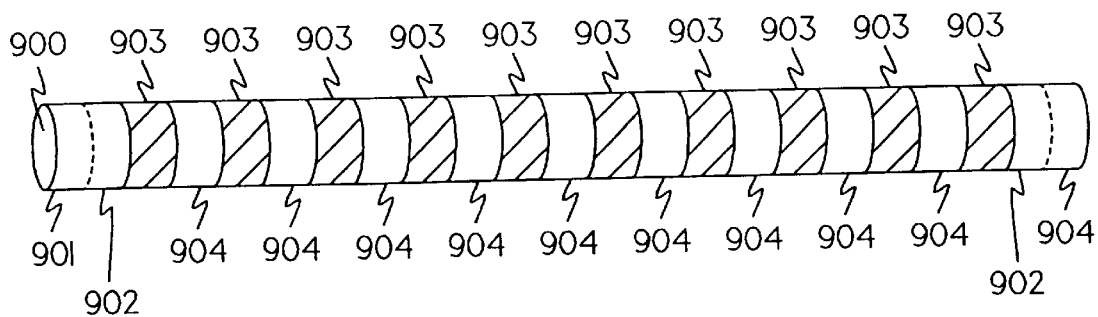
FIG. 11 is a schematic representation of an array of brachytherapy sources printed on a section of suture.

Using the method of this example, a 23-cm length of strand core can be gripped in the chucks using 1 cm of length at each end and held taut by the tensioning means. The chucks are positioned so that the surface of the strand core to be printed is always between 0.1 and 3 mm from the row of jets in the printhead nozzle plate, and the centerline of the strand core is in the plane formed by the trajectory of the drops. The synchronous motors are brought up to the speed of this example simultaneously so that the strand core is not twisted between the chucks. The printhead can now be used to deposit a radioactive fluid in any pattern and activity desired. Obviously, the strand core could be printed so as to produce a continuous and uniform source of any length compatible with that of the strand core used. A more complex example of an advantageous pattern for deposition is illustrated in FIG. 11. Chuck grip 901 is used to hold strand core 900 in the printing position. Margin 902 is left on each end and 1-cm sections 903 are then printed leaving 1 cm non-radioactive sections 904 between each radioactive section. If desired, radiopaque markers may be added by using conventional inkjet technology to print bands or lines of radiopaque ink such as, for example, those produced by Creative Materials Incorporated of Tyngsboro, Mass., USA. Radiopaque bands can also be applied by crimping appropriately sized bands of an X-ray absorbing material such as gold or platinum around the strand core at desired locations. Such bands are preferably applied before depositing the radioactive material. If the radioactive fluid of Example 3 is used and 6,045 drops are deposited into each printed section, each radioactive section will have an activity of approximately 6 millicurie of Pd-103. A source of energy may then be used to accelerate or trigger drying or curing of the layer of radioactive material. A radiation detector may be used to assay or measure the radioactivity of each section of the strand core. A protective coating may be applied, for example by dipping the strand core into a suitable plastic fluid, which subsequently dries or cures to form the coating. Alternately, an apparatus identical to that depicted in FIG. 10, with the exception that a jettable coating fluid is used instead of a radioactive jettable fluid, may be used to apply a protective coating to the strand.

Example 5

The method disclosed herein may also be employed to apply radioactive material to a sheet of plastic material. Such a sheet can be positioned at a surgical margin following removal of a malignant tumor in order to kill any remaining cancer cells. Such a device may be made of any biocompatible material including a biodegradable plastic so that, after the radioactive isotope decays to an insignificant level, the sheet is dissolved by the physiological action of bodily fluids. "Biocompatible material," as used herein, means a material that elicits no overt biological reaction in the body in which such material is placed. Biocompatible materials of the present invention do not elicit immune reactions, inflammatory reactions or other similar reactions. Certain biocompatible materials of the present invention are however degradable by the body by solubilization, by macrophage activity or by other naturally present digestive processes.

Figure 12:
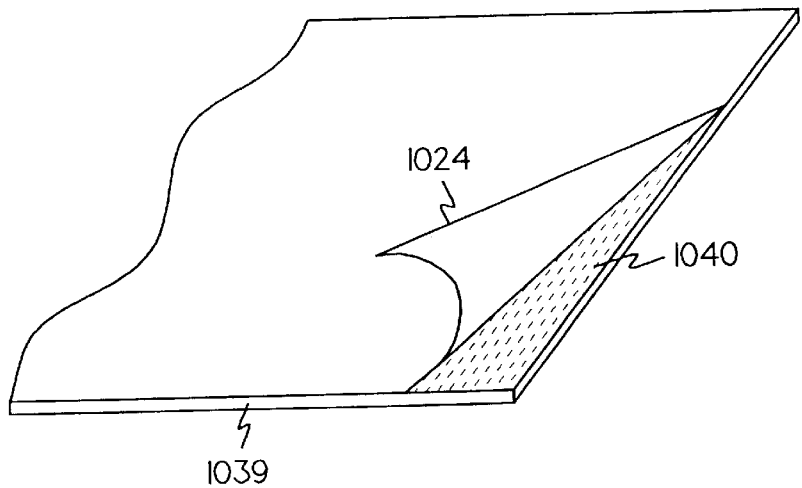
FIG. 12 is a schematic representation of a therapeutic radioactive sheet produced in accordance with the present invention.

A sheet brachytherapy-device produced in accordance with the present embodiment of the invention provides a uniform radiation field at planes parallel to the sheet. FIG. 12 illustrates a portion of a sheet embodiment of such therapeutic material. A supporting layer 1039, a layer of printed radioisotope 1040 and a protective layer 1024 are shown.

Figure 13:
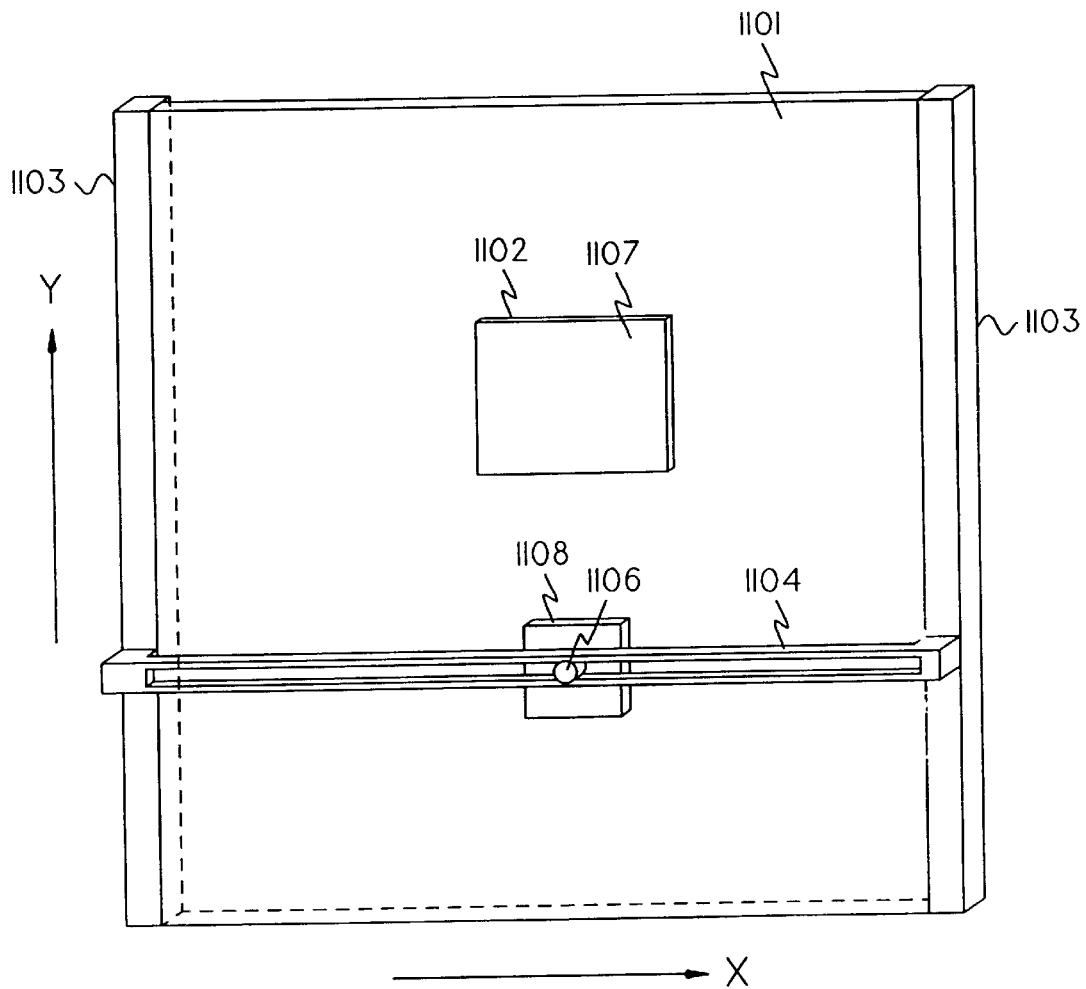
FIG. 13 is a schematic representation of an apparatus for depositing radioactive material on a planar substrate such as the sheet of FIG. 12.

The apparatus required for the preparation of a sheet embodiment of the present invention example is illustrated in FIG. 13. A positioning surface 1101 positions support layer 1102 so that the upper surface 1107 of support layer 1102 is parallel to and 0.1 to 3 mm from the plane of nozzle plate (not shown) of printhead 1108. X and Y positioners 1104 and 1103 respectively cause the printhead 1108 to be positioned and moved over any portion of the support layer 1102. Z positioner 1106 allows the distance between the nozzle plate (not shown) of printhead 1108 and upper surface 1107 of support layer 1102 to be adjusted to between 0.1 and 3 mm. Optionally, the apparatus may also incorporate a printing or other system for providing radiopaque markings, an assay means, an observing means such as a monitoring video camera to verify printhead performance and a drying or curing means such as an air or heat source. A means for applying a protective layer may also be provided. For example, means for applying a liquid that dries or cures to form a protective layer may comprise a printing means, a painting means, a spraying means, or a dipping means. A protective layer may also be applied by attaching a film with an adhesive layer over the radioactive layer.

Using the radioactive fluid of Example 3 and the MIT printhead of Example 1, a 1-cm square area of support layer can be printed using the apparatus of FIG. 13. For example, if the desired activity in this area is 6 millicurie, then 6045 drops would be deposited. This can be accomplished by using 14 adjacent jets of the MIT printhead to print five side-by-side strips, each 2 mm wide and 10 mm long. This is achieved with forty-five columns, each containing eighty-six drops, and twenty-five columns, each containing eighty-seven drops.

Having described the invention in detail and by reference to the preferred embodiments thereof, it will be apparent to those of skill in the art that modifications and variation are possible without the departing from the spirit, or exceeding the scope, of the disclosed invention. The components, methods, procedures and techniques described herein, as illustrated by reference to the preceding disclosure, are intended to be exemplary, and are not intended to limit the scope of the present invention. Those of skill in the art will readily appreciate that the present invention is well adapted to carry out the objects and obtain the ends and advantages mentioned, as well as those inherent therein. Changes in the components, methods, procedures and techniques described herein and other uses for the invention will occur to those skilled in the art. For example radioactive devices for use other than medical treatment may also be produced in accordance herewith. It will be appreciated that all such changes and other uses are encompassed within the spirit of the invention and the scope of the appended claims. All patents and publications cited anywhere in this document are incorporated by reference in their entirety; however all terms defined or as used herein prevail over any conflicting definitions or usages in such references.

What is claimed is:

1. An apparatus for depositing discrete dots of radioactive material onto a surface of a substrate, said apparatus comprising:
   (a) a fluid-jet printhead;
   (b) a reservoir adapted for containing and dispensing radioactive fluid, having an opening communicating with said fluid-jet printhead;
   (c) means for positioning and repositioning said printhead relative to the substrate;
   (d) computing means, in communication with said printhead and with said positioning means (c), for controlling relative positions of said printhead and the substrate, and for controlling fi of said printhead, so as to apply predetermined amounts of said radioactive fluid onto said substrate at predetermined positions; and (e) means for measuring the radioactivity; and (f) computing means, receptive to data supplied by said measuring means (e) and controlling the amount of radioactive fluid subsequently deposited by said printhead in accordance with said data.

2. An apparatus for depositing discrete dots of radioactive material onto a surface of a substrate, said apparatus comprising:

(a) a fluid-jet printhead;

(b) a reservoir adapted for containing and dispensing radioactive fluid, having an opening communicating with said fluid-jet printhead;

(c) means for positioning and repositioning said printhead relative to the substrate;

(d) computing means, in communication with said printhead and with said positioning means (c), for controlling relative positions of said printhead and the substrate, and for controlling firing of said printhead, so as to apply predetermined amounts of said radioactive fluid onto said substrate at predetermined positions;

(e) means for measuring the radioactivity that has been applied to a substrate; and (f) computing means, receptive to data supplied by said measuring means (e) and providing feedback to said computing means (d), for controlling the amount of radioactive fluid subsequently deposited by said printhead.

3. The apparatus of claim 1, further comprising:

(g) curing means for curing said radiation resistant curable liquid by applying heat, irradiation or catalysis to said substrate.

4. An apparatus for depositing discrete dots of radioactive material onto a surface of a substrate, said apparatus comprising:

(a) a fluid-jet printhead;

(b) a reservoir adapted for containing and dispensing radioactive fluid, having an opening communicating with said fluid-jet printhead;

(c) means for positioning and repositioning said printhead relative to the substrate;

(d) computing means, in communication with said printhead and with said positioning means (c), for controlling relative positions of said printhead and the substrate, and for controlling firing of said printhead, so as to apply predetermined amounts of said radioactive fluid onto said substrate at predetermined positions; and (e) coating means to apply over said substrate so as to sealingly enclose the radioactive material, a coating that is substantially transparent to the radiation of said radioactive fluid.

5. The apparatus of claim 1, wherein the radioactive fluid comprises:

a radioactive isotope; and a rapidly curable radiation-resistant curable liquid.

6. The apparatus of claim 5, wherein said radiation-resistant curable liquid comprises a binder.

7. The apparatus of claim 6, wherein said binder is an acrylic resin or sodium silicate.

8. The apparatus of claim 5, wherein:

said radioactive isotope is in the form of:

(a) a solution of a radioactive complex, (b) a solution of a radioactive salt, (c) a radioactive isotope adsorbed onto a powder, or (d) a powder consisting essentially of radioactive and nonradioactive isotopes of an element.

9. The apparatus of claim 1, wherein said radioactive fluid comprises a solution of $(NH_3)_4Pd(OH)_2$.

10. The apparatus of claim 1 wherein said radioactive fluid comprises a powder having radioactive iodine or radioactive palladium absorbed thereto.

11. An apparatus for depositing discrete dots of radioactive material onto a surface of a substrate, sad apparatus comprising:

(a) a fluid-jet printhead;

(b) a reservoir adapted for containing and dispensing radioactive fluid, having an opening communicating with said fluid-jet printhead;

(c) means for positioning and repositioning said printhead relative to the substrate;

(d) computing means, in communication with said printhead and with said positioning means (c), for controlling relative positions of said printhead and the substrate, and for controlling firing of said printhead, so as to apply predetermined amounts of said radioactive fluid onto said substrate at predetected positions in response to a sensed amount of radioactivity.

12. The apparatus of claim 11, further comprising:

(g) curing means for curing said radiation resistant curable liquid by applying heat, irradiation or catalysis to said substrate.

13. The apparatus of claim 11, further comprising:

(h) coating means to apply over said substrate so as to sealingly enclose the radioactive material, a coating that is substantially transparent to the radiation of said radioactive fluid.

14. The apparatus of aim 11, wherein the radioactive fluid comprises:

a radioactive isotope in the form of (a) a solution of a radioactive complex, (b) a solution of a radioactive salt, (c) a radioactive isotope adsorbed onto a powder, or (d) a powder consisting essentially of radioactive and nonradioactive isotopes of an element; and a rapidly curable radiation-resistant curable liquid.

* * * * *